United States Patent [19]

Sakai et al.

[11] Patent Number: 4,937,048
[45] Date of Patent: Jun. 26, 1990

[54] CARRIER TRANSPORTING APPARATUS AND CARRIER CONTAINER FOR USE IN AN IMMUNOLOGICAL ANALYSIS

[75] Inventors: Masahiko Sakai, Hachioji; Hiroshi Takekawa; Takashi Yamada, both of Sagamihara; Shirou Ishiwatari, Hino, all of Japan

[73] Assignee: Olympus Optical Company Limited, Tokyo, Japan

[21] Appl. No.: 575,149

[22] Filed: Jan. 30, 1984

[30] Foreign Application Priority Data

Jan. 31, 1983 [JP] Japan .............................. 58-11200[U]
Jan. 31, 1983 [JP] Japan .............................. 58-11222[U]
Jan. 31, 1983 [JP] Japan .............................. 58-11223[U]

[51] Int. Cl.$^5$ ........................................... G01N 35/06
[52] U.S. Cl. ........................................ 422/63; 422/65; 422/67; 422/73
[58] Field of Search ............... 414/737, 744, 304, 186, 414/752, 627; 221/93, 95, 135, 298, 263–265; 422/67, 65, 73, 100, 102, 63; 435/227, 317

[56] References Cited

U.S. PATENT DOCUMENTS

| | | | |
|---|---|---|---|
| 3,101,872 | 8/1963 | Dickinson | 221/265 |
| 3,764,267 | 10/1973 | Farr | 422/81 |
| 3,912,452 | 10/1975 | Sodickson et al. | 422/81 |
| 3,932,141 | 1/1976 | Beall et al. | 422/102 |
| 4,101,284 | 7/1978 | Difiglio et al. | 422/100 |
| 4,150,766 | 4/1979 | Westendorf et al. | 221/265 |
| 4,261,681 | 4/1981 | Gates | 414/744 B |
| 4,364,707 | 12/1982 | Ott | 414/737 |
| 4,383,041 | 5/1983 | Kutsusawa et al. | 422/65 |
| 4,405,060 | 9/1983 | Hsei | 221/135 |
| 4,415,098 | 11/1983 | Haas | 221/264 |
| 4,419,041 | 12/1983 | Rose | 414/729 |
| 4,437,232 | 3/1984 | Araki et al. | 414/744 B |
| 4,444,598 | 4/1984 | Sakagami | 422/81 |
| 4,482,521 | 11/1984 | Bunce et al. | 436/809 |

FOREIGN PATENT DOCUMENTS 433664 9/1926 Fed. Rep. of Germany ...... 221/298
563628 5/1975 Switzerland ........................ 221/298

Primary Examiner—Michael S. Marcus
Attorney, Agent, or Firm—Stevens, Davis, Miller & Mosher

[57] ABSTRACT

A carrier transporting apparatus for use in an automatic chemical analyzer for measuring given substances in samples in accordance with an enzyme-immuno-assay includes a carrier supply device for supplying the predetermined number of carriers from a carrier container into successive reaction vessels and a carrier discharge device for discharging the carriers from the reaction vessels, in a simple and accurate manner. Moreover, the carrier container from which the carriers can be put out one by one in an accurate manner is also disclosed.

8 Claims, 7 Drawing Sheets

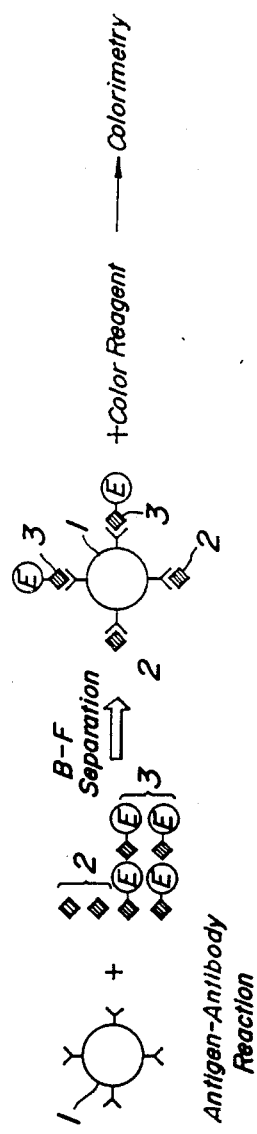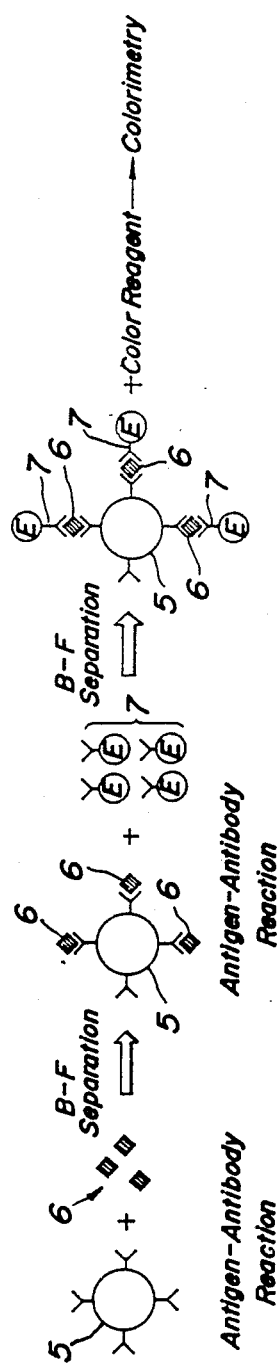

CARRIER TRANSPORTING APPARATUS AND CARRIER CONTAINER FOR USE IN AN IMMUNOLOGICAL ANALYSIS

BACKGROUND OF THE INVENTION

The present invention relates to a carrier transporting apparatus for use in an immunological analysis which supplies and/or discharges the predetermined number of carriers into and/or from successive reaction vessels.

Nowadays, due to the progress in medical treatment, very small amounts of biological substances in samples can be analyzed and this contributes to early diagnosis for various diseases. For instance, malignant tumors which may be detected by measuring an abnormal increase of α-fetoprotein and carcinoembryonic antigen, diseases caused by abnormal secretions of hormones such as insulin and thyroxine, and immunological diseases caused by an abnormal increase or decrease of immunoglobulin can be diagnosed in early stages by means of biochemical analysis. Further, monitoring after treatments for these diseases can be carried out reliably. Moreover, the measurement of incomplete antigens, i.e. low molecular hapten of medical substances contributes to the development of a plan of medication.

Many biological substances are analyzed in an immunological manner by utilizing the antigen-antibody reaction and various methods for effecting the immunological analysis have been developed.

In one of well-known methods, there has been developed a method which utilizes antigen or antibody coupled with labeling material which detects antigen-antibody compounds at a high sensitivity.

The analytic methods using the markers are classified into radio-immuno-assay using radioisotope tracers, fluorescent-immuno-assay using fluorescent labeling material, and enzyme-immuno-assay using enzyme markers. Among these methods, the enzyme-immuno-assay has been particularly developed owing to the reason that it does not require special installation and measuring techniques and can be performed easily by using commonly developed colorimeters. The enzyme-immuno-assay is further classified into homogeneous enzyme-immuno-assay and heterogeneous enzyme-immuno-assay. In the homogeneous analysis, a variation in activity of labeling enzyme due to existence or non-existence of the immunological reaction is directly measured to detect substances to be analyzed. In the heterogeneous analysis, use is made of insoluble carriers such as glass beads or synthetic resin particles on which antigen or antibody has been fixed, enzyme-labeled antigen or antibody bound with the antibody or antigen fixed on the carriers and free enzyme-labeled antigen or antibody not bound with the antibody or antigen on the carriers are separated from each other by washing treatment, and then an activity of labeling enzyme is detected to measure a quantity of substances to be analyzed. Hereinbelow, the process for separating the bound antigen or antibody and the free antigen or antibody from each other is termed as B-F separation for the sake of simplicity. Although the homogeneous analysis can be performed by simple processes, it can analyze only the low molecular hapten such as medical substances, but cannot analyze high molecular biological substances. Contrary to this, in the heterogeneous analysis, although the washing process is required for effecting the B-F separation, it can be applied to any kinds of low and high molecular substances. Therefore, recently the heterogeneous enzyme-immuno-assay has been generally adopted.

In the heterogeneous enzyme-immuno-assay, there have been developed competitive method and sandwich method. Now these methods will be explained with reference to the drawings.

FIG. 1 illustrates successive steps of the competitive method. A given antigen or antibody which reacts with antibody or antigen substances 2 of a sample has been previously fixed to an outer surface of a insoluble carrier 1. At first, the antigen-antibody reaction is carried out between the antigen or antibody fixed onto the carrier 1 and the antibody or antigen 2 in the sample as well as a labeled reagent 3 which has been prepared by labeling substances which are the same as the substances 2 to be analyzed with enzyme marker. Then, a washing process is carried out to effect the B-F separation between the substance 2 and labeled reagent 3 bound with the carrier 1 due to the antigen-antibody reaction and free substances 2 and reagent 3 which are not bound with the carrier 1. Next, a color reagent which selectively reacts with the labeling enzyme is added and a reaction liquid is colorimetered to detect the enzyme activity of the labeling enzyme.

FIG. 2 shows successive steps of the sandwich method in which use is made of an insoluble carrier 5 having fixed thereto antibody or antigen which is reactive with antigen or antibody substances in a sample to be tested. At first, the carrier 5 and the sample 6 are mixed to effect the antigen-antibody reaction between the substances 6 in the sample and the antibody or antigen fixed to the carrier 5. Then, the B-F separation is carried out by means of the washing step. Next, a labeled reagent 7 is added to effect the antigen-antibody reaction. The labeled reagent is prepared by marking it with an enzyme substance selectively reactive with the substance 6 to be analyzed. Then, after the B-F separation is effected again, a color reagent reacting with the labeling enzyme in the labeled reagent 7 is added and a test liquid thus obtained is colorimetered to detect the activity of the labeling enzyme.

Usually, these competitive method and sandwich method have been performed by a manual operation. In this case, many carriers contained in a carrier container are supplied into the reaction vessel one by one by the manual operation and also the carrier supplied in the reaction vessel is manually discharged from the reaction vessel after the end of the analysis for the sample. However, in the automatic analyzer which performs automatically the immunological analysis, it is necessary to supply and/or discharge the carriers automatically into and/or from successive reaction vessels one by one in a precise manner.

SUMMARY OF THE INVENTION

The present invention has for its object to eliminate the drawbacks mentioned above and to provide a carrier transporting apparatus which can supply and/or discharge the predetermined number of carriers into and/or from successive reaction vessels in a precise manner by a simple construction.

According to the invention, a carrier transporting apparatus for use in an automatic analyzer which analyzes given substances in samples in an immunological manner comprises:

means for supplying a given number of carriers into successive reaction vessels; and means for discharging said carriers from said reaction vessels after analysis.

The present invention also relates to a carrier container for use in the above apparatus and has for its object to provide a novel carrier container for use in an immunological analysis from which the carrier can be removed one by one in an accurate manner.

According to the invention, a carrier container for use in a carrier transporting apparatus of an automatic analyzer which analyzes given substances in samples in an immunological manner comprises:

a hopper for holding a number of carries therein;

a passage having an inlet connected to a lower end of the hopper, an outlet opening upwardly and a linear portion connected to the outlet and extending substantially in a horizontal direction, said carriers being aligned along the passage; and a stop means arranged uprightly at the outlet for limiting a horizontal movement of along the passage carriers.

BRIEF DESCRIPTION OF THE DRAWINGS

FIG. 1 is a schematic view showing successive steps of a known competitive method;

FIG. 2 is a schematic view illustrating successive steps of a known sandwich method;

DETAILED EXPLANATION OF THE PREFERRED EMBODIMENTS

Figure 3:
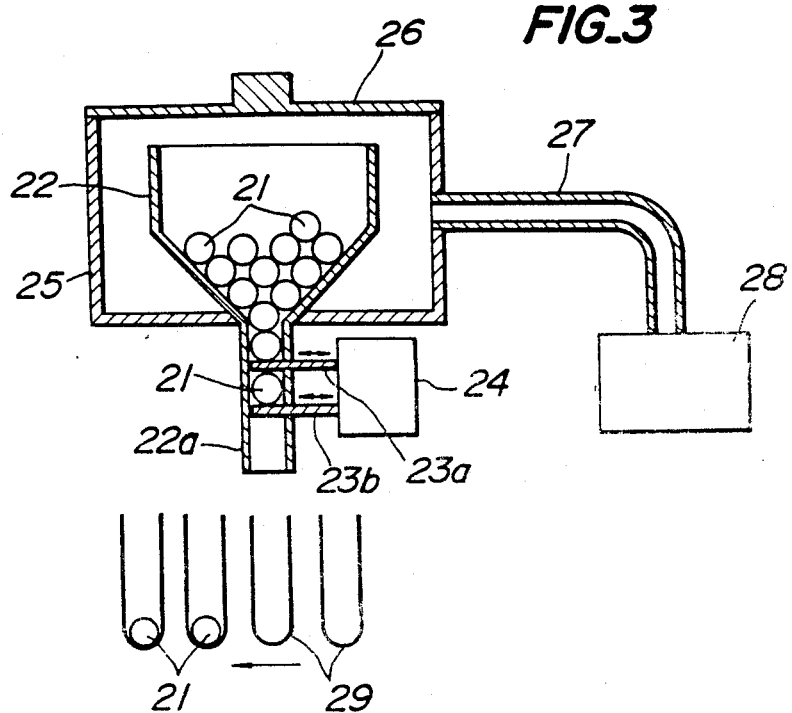
FIG. 3 is a cross sectional view depicting one embodiment of a carrier supply device for use in the carrier transporting apparatus according to the invention.

FIG. 3 is a cross sectional view showing an embodiment of the carrier transporting apparatus embodied as the carrier supply device. In the present embodiment, a number of carriers 21 having given antibody or antigen fixed thereto are contained in a carrier container 22 in the form of a hopper. At the lower end of the carrier container 22 is provided an outlet passage 22a through which the carrier 21 can be passed. In the outlet passage 22a there are formed a pair of recesses in which a pair of gate plates 23a and 23b are inserted slidably. In the present embodiment, the carriers 21 are to be supplied into reaction vessels 29 one by one, so that the gate plates 23a and 23b are separated from each other by such a distance that only a single carrier 21 can situate therebetween. It should be noted that if two carriers are to be supplied into each reaction vessel, the gate plates 23a and 23b should be separated from each other by a longer distance so that two carriers can exist therebetween. The gate plates 23a and 23b are selectively moved with respect to the outlet passage 22a by means of a gate plate driving device 24 comprising solenoids. The container 22 is arranged in a housing 25 having an upper opening which is closed by a lid 26. In case of supplementing the carriers 21 into the container 22, the lid 26 is removed. The housing 25 communicates by means of a duct 27 with a humidifier 28 so as to keep a humidity within the housing 25 at a given constant value. As explained above the antibody or antigen fixed onto the surface of carrier 21 is composed of protein which might be modified in a non-reversible manner due to atmospheric conditions such as PH, temperature and humidity.

In the carrier supply device of the present embodiment, in a rest condition shown in FIG. 3, both the gate plates 23a and 23b are projected into the outlet passage 22a and one carrier 21 is held between the plates 23a and 23b. At a suitable timing, the lower gate plate 23b is withdrawn from the passage 22a and the carrier 21 is dropped into a reaction vessel 29 due to the gravitational force. Then, after the gate plate 23b has been inserted into the passage 22a, the upper gate plate 23a is withdrawn from the passage 22a. Then, a carrier 21 moves downward until it is brought into contact with the gate plate 23b. Finally, the gate plate 23a is inserted into the passage 22a. In this manner, the carriers 21 can be positively supplied into the reaction vessels 29 one by one.

Figure 4:
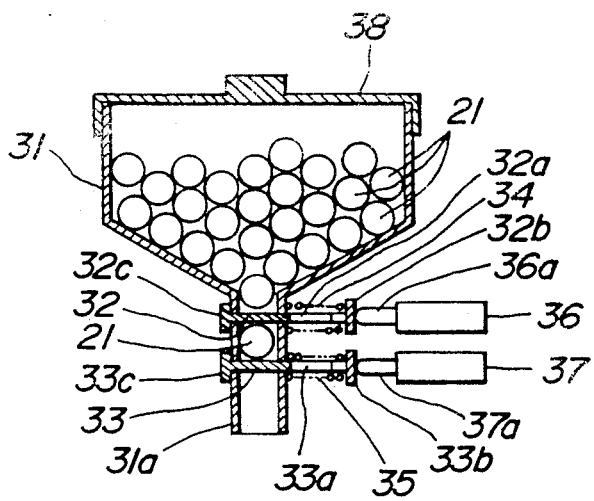
FIGS. 4 and 5 are a cross sectional and a perspective views showing another embodiment of the carrier supply device according to the invention.
Figure 5:
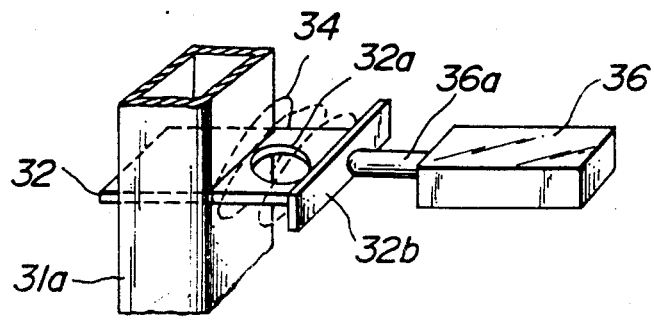

FIGS. 4 and 5 illustrate a modification of the embodiment of the carrier supply device shown in FIG. 3. In a present embodiment, a container for holding a number of carriers is formed as a cassette which can be detachably secured to a housing. The container 31 in the form of cassette has an outlet passage 31a integrally formed at a lower end thereof and a pair of gate plates 32 and 33 are arranged in the outlet passage 31a movably in a direction perpendicular to an axis of the outlet passage 31a. In the gate plates 32 and 33 is formed holes 32a and 33a, respectively having a diameter larger than that of the carrier 21. At both side edges of the gate plates 32 and 33 are secured stop members 32b, 32c and 33b, 33c, respectively. Between the outlet passage 31a and the stop members 32b and 33b are arranged coil springs 34 and 35, respectively so as to bias the gate plates rightward in FIG. 4. This rightward movement of the gate plates 32 and 33 is limited by the stop members 32c and 33c. In a main body, there are further provided solenoids 36 and 37 whose plungers 36a and 37a are urged against the stop members 32b and 33b, respectively. In FIG. 5, for the sake of clarity the coil spring 34 is shown by a broken line. An upper opening of the carrier container 31 is closed by a lid 38.

When the carrier container 31 is installed into the main body, the stop members 32b and 33b are brought into positions opposite to the plungers 36a and 37a of solenoids 36 and 37, respectively. Then the solenoid 36 is energized to move the gate plate 32 leftward against the force of the coil spring 34 so that the hole 32a is aligned with the outlet passage 31a. Therefore, a carrier 21 is passed through the hole 32a and is placed on the gate plate 33. Then the solenoid 36 is de-energized and the gate plate 32 is moved leftward due to the action of the coil spring 34. In this manner, the single carrier 21 can be introduced into a space defined by the gate plates 32 and 33. At a suitable timing, the solenoid 37 is energized and the gate plate 33 is pushed into the outlet passage 31a. Then, the carrier 21 is passed through the hole 33a formed in the gate plate 33 and is dropped into a reaction vessel. In this manner, the carriers 21 can be supplied into the reaction vessels one by one in an accurate manner.

Figure 6:
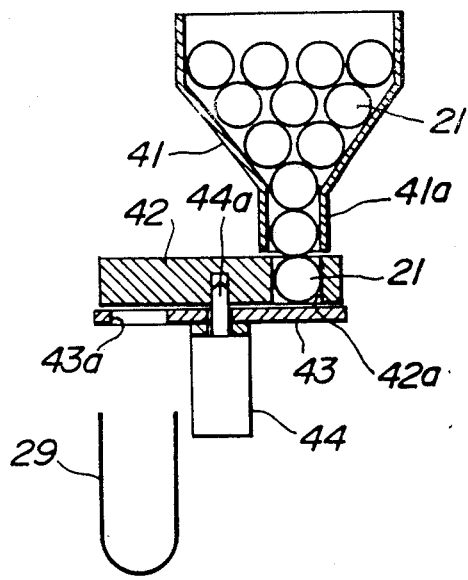
FIG. 6 is a cross sectional view illustrating still another embodiment of the carrier supply device according to the invention.

FIG. 6 is a cross section depicting another embodiment of the carrier supply device according to the invention. In the present embodiment, a number of carriers 21 are contained in a container 41 in the form of the hopper and an outlet passage 41a is integrally formed with the container 41 at its lower end. Underneath the outlet passage 41a is arranged rotatably a gate disc 42 and a hole 42a is formed at its periphery. As shown in FIG. 6, hole 42a has a diameter which is slightly larger than a diameter of the carrier 21 and a thickness of the gate disc 42 is slightly larger than the diameter of the carrier 21. Therefore, as shown in FIG. 6, the gate disc 42 can be rotated, while one carrier 21 is held in the hole 42a. Underneath the gate plate 42 is arranged a stationary disc 43 and a hole 43a having a diameter larger than the diameter of the carrier 21 is formed in the stationary disc 43 at its periphery. On the lower surface of the stationary disc 43 is secured a rotary solenoid 44 whose plunger 44a is connected to the rotary gate disc 42 via the stationary disc 43. In a condition shown in FIG. 6, the single carrier 21 has been dropped into the hole 42a of the gate disc 42. When the rotary solenoid 44 is energized to rotate the gate disc 42 by 180 degrees, the hole 42a in the gate disc 42 is aligned with the hole 43a in the stationary disc 43 and thus the carrier 21 is dropped into a reaction vessel 29 through the hole 43a. After that, when the rotary solenoid 44 is de-energized, the gate disc 42 is rotated by 180 degrees in a reverse direction and a carrier 21 is dropped into the hole 42a in the gate plate 42. In this manner, the carriers 21 can be supplied into the reaction tubes 29 one by one.

Figure 7:
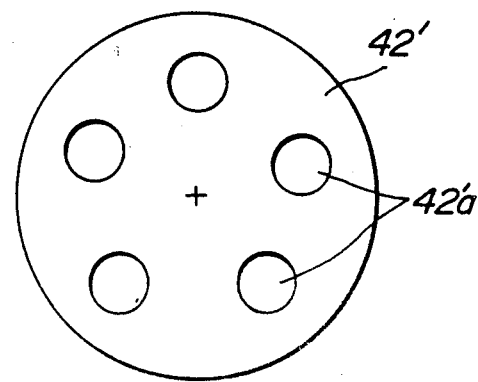
FIG. 7 is a plan view depicting one embodiment of a gate disc according to the invention.

FIG. 7 is a plan view showing a modified embodiment of the gate disc. In the present embodiment, the gate disc 42' has five holes 42a' equidistantly arranged along the periphery of the gate disc. Therefore, by rotating the gate disc 42' by angle equal to 1/5×360°, the carriers can be successively supplied into the reaction vessels one by one.

Figure 8:
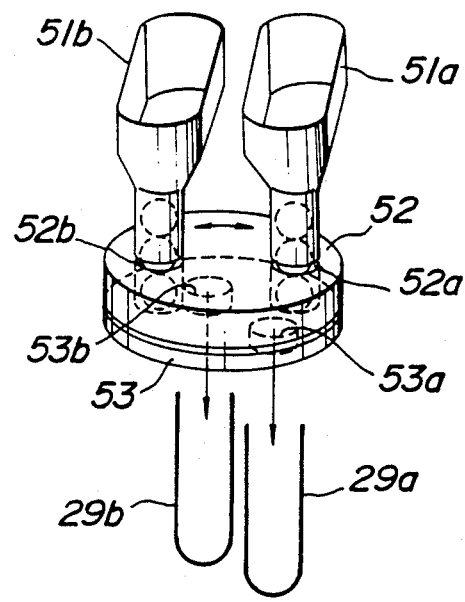
FIG. 8 is a perspective view showing still another embodiment of the carrier supply device according to the invention.

FIG. 8 is a perspective view illustrating a modification of the embodiment of the carrier supply device shown in FIG. 6. The device of the present embodiment can be advantageously used to supply two kinds of carriers. Underneath a pair of carrier containers 51a and 51b is arranged rotatably a gate disc 52. In the gate disc 52 there are formed a pair of holes 52a and 52b at diametrically opposite positions. Underneath the gate disc 52 is arranged a stationary disc 53 in which are formed a pair of holes 53a and 53b at diametrically opposite positions. In a condition illustrated in FIG. 8, each of the holes 52a and 52b holds one carrier. By rotating the gate disc 52 in a clockwise direction, the holes 52a and 52b are aligned with the holes 53a and 53b, respectively and the carriers are dropped into reaction tubes 29a and 29b, respectively. In this manner, two kinds of carriers can be supplied into the reaction vessels one by one in an efficient manner.

Figure 9:
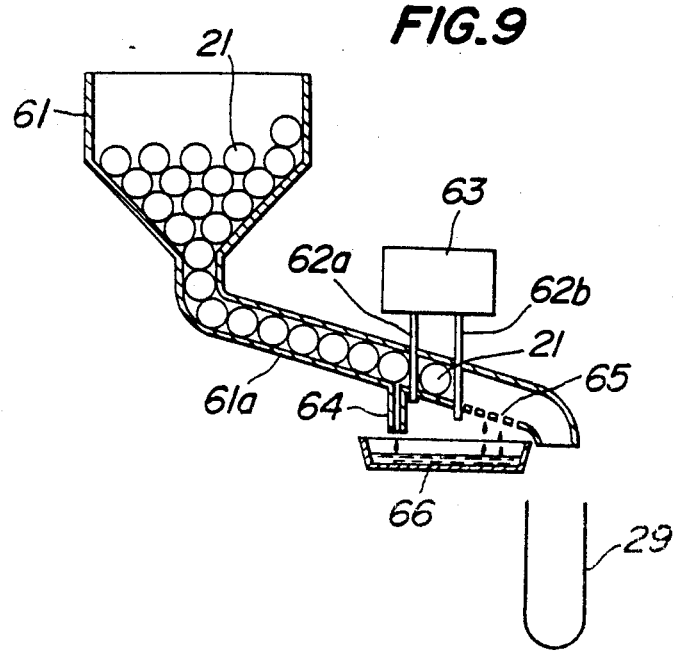
FIG. 9 is a cross sectional view illustrating still another embodiment of the carrier supply device according to the invention.

FIG. 9 is a cross sectional view depicting still another embodiment of the carrier supply device according to the invention. In the present embodiment, at a lower end of a container 61 in the form of a hopper is arranged a long outlet passage 61a which is inclined downward as shown in the drawing. At a middle of the outlet passage 61a are arranged slidably a pair of gate plates 62a and 62b which are moved with respect to the outlet passage 61a by means of a driving device 63 containing solenoids. As explained above, the antibody or antigen layer fixed onto the surfaces of carriers 21 are wetted with a buffer solution so as to prevent the antibody or antigen from being modified. Therefore, the buffer solution might be dropped into reaction vessels 29 via the outlet passage 61a and this might affect the analysis. In order to avoid such a drawback, in the outlet passage 61a are provided a drain 64 and a mesh portion 65 so as to collect the buffer solution flowing along the outlet passage into a tray 66. By means of the carrier supply device of the present invention, it is possible to supply the carriers 21 into the reaction vessels 29 one by one, while the buffer solution for wetting the carriers can be effectively prevented from being dropped into the reaction vessels.

Figure 10:
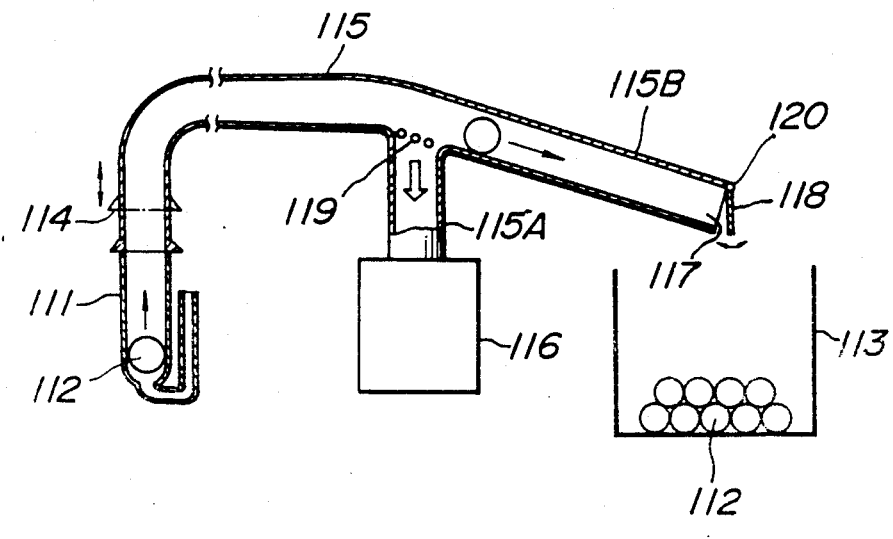
FIG. 10 is a schematic view showing one embodiment of a carrier discharge device for use in the carrier transporting apparatus according to the invention.

FIG. 10 is a schematic view showing one embodiment of a carrier discharging device for use in the carrier transporting apparatus according to the invention. In this embodiment, a carrier 112 supplied in a U-shaped reaction tube 111 having a large and small mouth portions is sucked into a carrier discharge container 113 by using a negative pressure. Therefore, one end of a suction tube 115 is detachably connected to an opening portion of the U-shaped tube 111 through an elastic mouth portion 114 by means of a driving means not shown. The other end of the suction tube 115 is inclined downward and is divided into two end portions 115A and 115B. The one end portion 115A is connected to a suction pump 116 and an outlet 117 to the other end portion 115B is faces to the carrier discharge container 113. Further, as shown in FIG. 10, a bellows 118 which functions to open and close the outlet 117 is journalled to the outlet 117 by means of a hinge 120. Moreover, a guide member 119 such as a mesh is arranged at the divided portion 115A of the suction tube 115 not to supply the sucked carrier to the end portion 115A but to introduce it to the end portion 115B. In the carrier discharging device mentioned above, after the suction tube 115 is connected to the U-shaped tube 111 through the mouth portion 114 and the suction pump 116 is energized, the outlet 117 of the suction tube 115 is closed by the bellows 118 so that the carrier 112 contained in the U-shaped tube 111 is transported to the divided portion in the suction tube 115. After that, the suction pump 116 is de-energized and the outlet 117 is opened by rotating the bellows 118 about the hinge 120, so that the carrier positioned at the divided portion is thrown down into the carrier discharge container 113 through the outlet 117.

Figure 11A:
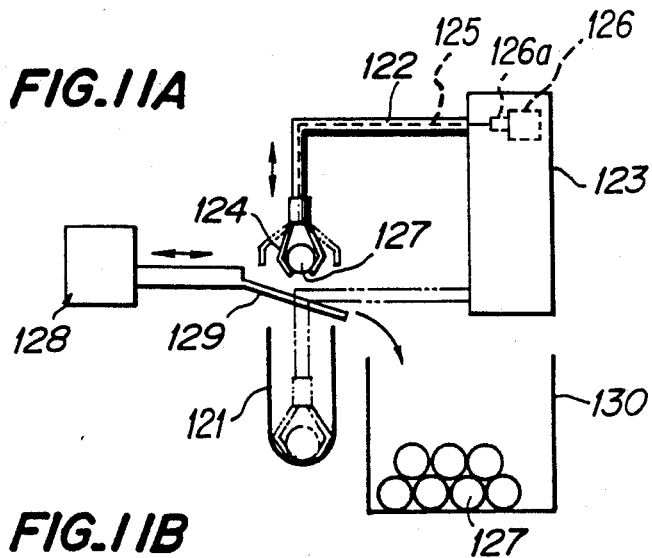
FIGS. 11A and 11B are schematic views illustrating another embodiment of the carrier discharge device according to the invention.
Figure 11B:
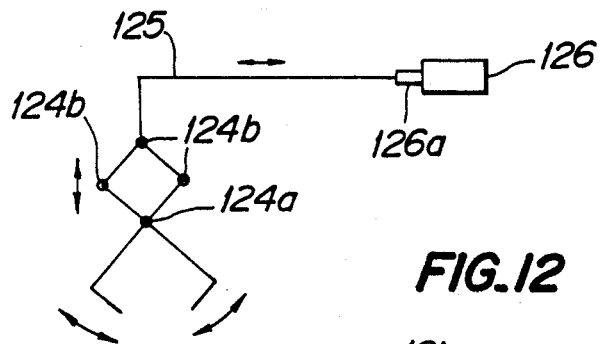

FIGS. 11A and 11B are schematic views showing another embodiment of the carrier discharging device according to the invention. In this embodiment, an arm 122 is arranged to ascend and descend selectively by means of an arm elevator 123. In addition, a carrier holding member 124 which can hold a carrier 127 is arranged at a tip portion of the arm 122, so that the holding member 124 can be intruded in a reaction tube 121. As shown in FIG. 11B in detail, the carrier holding member 124 is constituted by a pantagraph construction including a fix fulcrum 124a and movable fulcrums 124b. In the carrier holding member 124, a wire 125 is extended along the arm 122 between the movable fulcrum 124b opposed to the fixed fulcrum 124a and a plunger 126a of a solenoid 126 moved up and down together with the arm 122. Therefore, the carrier holding member 124 is opened and closed in response to on and off operations of the solenoid 126.

In the embodiment shown in FIGS. 11A and 11B, at first the arm 122 is moved downward to a predetermined position by means of the arm elevator 123 after the solenoid 126 is de-energized to open the carrier holding member 124. Then, the solenoid 126 is energized to close the carrier holding member 124, and thus the carrier 127 in the reaction vessel 121 is held by the carrier holding member 124. After that, the arm 122 is moved upward by means of the arm elevator 123 to remove carrier 127 from the reaction vessel 121. Then, a slant plate inserting device 128 is energized to insert a slant plate 128 into an ascending path along which arm 122 is moved and then the solenoid 126 is de-energized to open the carrier holding member 124, so that the carrier 127 held by the carrier holding member 124 is thrown down on the slant plate 129 and thus the carrier 127 is supplied into the carrier discharge container 130.

Moreover, various modifications can be applied to the embodiment mentioned above. For example, the waste carrier 127 can be thrown down directly into the carrier discharge container 130 without using the slant plate 129 by rotating the arm 122. Further, the open and close operations of the carrier holding member 124 can be effected by another means other than the solenoid 126.

Figure 12:
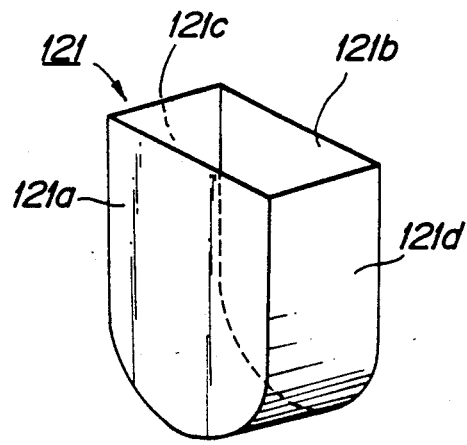
FIG. 12 is a perspective view depicting one embodiment of a reaction vessel which is preferably used for a direct photometry.

As clearly understood from the above, since the arm is moved up and down with respect to the reaction vessel and the carrier is removed from the reaction tube by the carrier holding member arranged at the tip portion of the arm, it is possible to remove accurately the carrier contained in the reaction vessel even if the reaction vessel has a different shape. Moreover, since only the carrier can be discharged from the reaction vessel in which a test liquid remains from the possible to effect the photometry directly through the reaction vessel. In case that the direct photometry is effected, use is made of a reaction vessel having a cylindrical bottom and a pair of opposite flat main surfaces 121a and 121b as shown in FIG. 12. In this case, the open and close operations of the carrier holding member are effected in a direction defined by a pair of cylindrical surfaces 121c and 121d, and the photometry is performed directly through the flat surfaces 121a and 121b.

Figure 13:
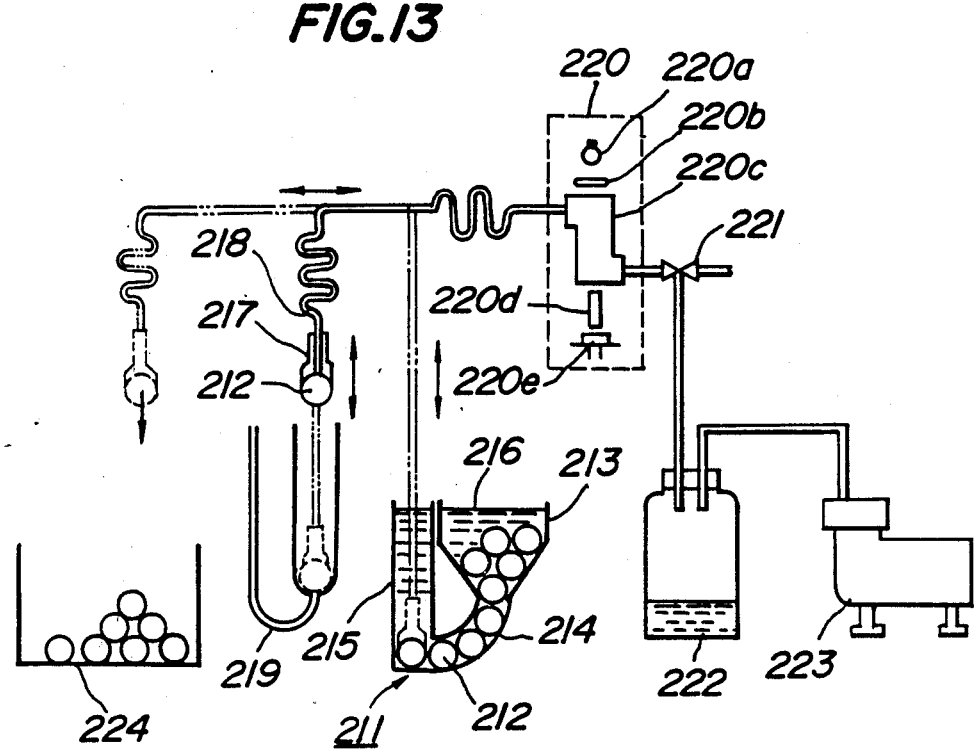
FIG. 13 is a schematic view showing one embodiment of the carrier transporting apparatus including the carrier container according to the invention.

FIG. 13 is a schematic view showing one embodiment of the carrier transporting apparatus including a carrier container according to the invention. In this embodiment, a carrier container 211 comprises a hopper 213 for holding a number of carriers 212. At a lower end of the hopper 213 is connected an inlet of a passage 214 having a curved portion and a flat portion. In this case, the carriers are rolled down into the passage 214 due to the gravitational force and are aligned therein. At an outlet of the passage 214 is arranged a vertical duct 215 for limiting the horizontal movement of carriers at a carrier discharge position. When the carrier 212 which is brought into contact with a vertical wall of the duct 215 at the carrier supply position is removed through the vertical duct 215, the next carrier is automatically positioned at the carrier supply position. Moreover, in this embodiment, the carriers 212 are dipped in a buffer solution 216.

Now, operations of the carrier transporting apparatus will be explained. A suction nozzle 218 having an elastic mouth portion 217 is arranged movably between the carrier suction position in the carrier container 211, carrier supply and suction positions in a reaction vessel 219 arranged at a given reaction line and a carrier discharge position in a carrier discharge container 224. Also at respective positions, the nozzle 218 is moved up and down. The suction nozzle 218 is selectively connected through a colorimeter 220 to the air or to a suction pump 223 through a three-directional valve 221 and a waste liquid tank 222. In the present embodiment, as the reaction vessel 219, use is made of a U-shaped tube having a large mouth portion and a small mouth portion, and the carrier 212 is supplied into the large mouth portion of the U-shaped tube 219. Therefore, a dimension of the carrier 212 is so determined as to be easily put in and out from the large mouth portion and not to be inserted into the small mouth portion.

Now, operation of the device according to the invention in the case that the carriers 212 are removed from the carriers container 211 one by one and the carriers 212 are supplied into successive U-shaped tubes 219 at the given carrier supply position will be explained with reference to FIG. 13. At first, a passage of the suction nozzle 218 to suction pumps 223 is closed by the valve 221, and then the suction nozzle 218 is moved to the carrier suction position through the vertical duct 215, so that the elastic mouth portion 217 is brought into contact with the carrier 212 positioned at the outlet of the passage 214. Under such a condition, the suction nozzle 218 is connected to the suction pump 223 through the three-directional valve 221 by changing the valve position thereof so as to suck and hold the carrier 212. After that, the suction nozzle is moved upward and then moved to the carrier supply position above the U-shaped tube 219. At this position, the passage of the suction nozzle 218 is connected to the air through the three-directional valve 221 by changing the valve position thereof, and then the carrier 221 held by the suction nozzle 218 is supplied to the U-shaped tube 219. When the carrier 212 which is brought into contact with the vertical wall at the carrier supply position is removed through the vertical duct 215, the next carrier is automatically positioned at the carrier supply position. Therefore, if the operation mentioned above is effected for the U-shaped tubes 219 successively transferred into the given carrier supply position in the reaction line, it is possible to put out the carriers 212 accurately from the carrier container 211 one by one and then to supply the thus removed carrier 212 into successive U-shaped tubes 219.

Now, proceeding operations after the completion of a predetermined immunological analysis will be explained. At first, the suction nozzle 218 is moved a little above the carrier discharge position in the U-shaped tube 219, and a test liquid in the U-shaped tube 219 is sucked by the suction nozzle 218 at that position into the colorimeter 220 after the nozzle 218 is connected to the suction pump 23 through the valve 221. After the test liquid is introduced into the colorimeter 220, the passage of the suction nozzle 218 is closed for a predetermined time period by the valve 221 to keep the test liquid in the colorimeter 220. During the time period, the colorimetry operation for the test liquid is effected. In the colorimeter 220, a light flux emitted from a light source 220a is projected through an interference filter 220b onto a flow cell 220c in which the test liquid is passed, and then a transmitted light flux is received by a light detector 220e through a light guide 220d. After the colorimetry, the passage of the suction nozzle 218 is connected again to the suction pump 223 by means of the valve 221, and at the same time the suction nozzle 218 is moved to the carrier suction position and is brought into contact or almost contact with the carrier 212 is the U-shaped tube 219. In the course of this operation, the test liquid remaining in the U-shaped tube 219 is discharged into the waste liquid tank 222 and then the carrier 212 is sucked and held by the suction nozzle 218. After that, the suction nozzle 218 is moved to the carrier discharge position in the carrier discharge container 224, and then the passage of the suction nozzle 218 is connected to the air by means of the valve 221 to discharge the waste carrier 212 transported from the U-shaped tube 219 into the carrier discharge container 224. Therefore, if the above operations are effected for all the U-shaped tubes containing the carrier 212 and test liquid, it is possible to effect the colorimetry operation for the test liquid contained in the U-shaped tube 219 and the discharging operation of the carrier 212.

Figure 14:
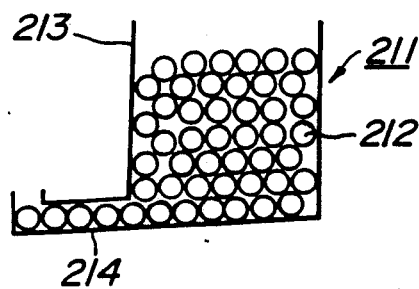
FIG. 14 is a schematic view illustrating another embodiment of the carrier container according to the invention.

Moreover, various modifications can be applied to the embodiment shown in FIG. 13. For example, in the embodiment shown in FIG. 13, the carrier supply position for the U-shaped tube 219, the colorimetry position and the carrier discharge position are set at the same position in the reaction line, but these positions can be arranged separately. Further, in this embodiment, the carriers 212 are dipped in the buffer solution 216, but it is not always necessary to dip the carriers 212 in the buffer solution 216. In this case, instead of arranging the vertical duct 215 it is possible to arrange a vertical wall at the outlet of the passage 214 for limiting the horizontal movement of carriers. In addition, it is not always necessary to remove the carrier 212 in a vertical direction and further to construct the passage 214 by the tube. Furthermore, in the embodiment shown in FIG. 13, the passage 214 of the carrier container 211 is constructed by the curved portion and the linear portion, but it is not always necessary to use the curved portion. For example, as shown in FIG. 14, it is possible to construct the passage 214 by only the linear portion arranged substantially in a horizontal direction. Moreover, the carrier container according to the invention can be effectively used for the manual operation.

As mentioned above, according to the invention, since one end of the passage for introducing successively the carriers substantially in the horizontal direction is connected to the lower end of the hopper for holding a number of carriers and at the other end of the passage is arranged a stop member for limiting the horizontal movement of carriers, it is possible to position automatically the carriers held in the hopper one by one at the outlet of the passage in the simple construction. Therefore, it is possible to removed the carriers one by one from the outlet of the passage in an easy and accurate manner.

As mentioned above in detail, according to the invention, it is possible to effect the carrier transporting operation in an easy and accurate manner and to make the apparatus simple in construction.

What is claimed is:

1. An apparatus for transporting a carrier for use in an automatic immunological analyzer, comprising:
    at least one reaction vessel;
    a suction tube having one end which is movable between a first position away from said reaction vessel and a second position near an opening of said reaction vessel; and
    a suction pump connected to said suction tube for applying a suction force to the suction tube sufficient to move a carrier contained in the reaction vessel out of the reaction vessel when said one end of the suction tube is in said second position, said one end of the suction tube comprising an elastic mouth which is detachably connected to an opening of the reaction vessel when said one end of the suction tube is in the second position, another end of the suction tube being divided into two divided end portions, the suction pump being connected to one of said divided end portions, and a bellows being provided at the other divided end portion for opening and closing an outlet of said other divided end portion in response to a suction operation.

2. An apparatus according to claim 1, further comprising a discharge container and wherein said other divided end portion is positioned to discharge a carrier into said discharge container.

3. An apparatus according to claim 1, wherein said bellows is journaled to said other divided end portion by a hinge.

4. An apparatus according to claim 1, wherein said divided end portions are inclined downward.

5. An apparatus according to claim 4, wherein a guide member is arranged at said one divided end portion of said suction tube to prevent a carrier from being introduced into said one divided end portion.

6. An apparatus according to claim 5, wherein said guide member comprises a mesh plate.

7. An apparatus for transporting a carrier for use in an automatic immunological analyzer, comprising:
    at least one reaction vessel;
    a suction tube having one end which is movable between a first position away from said reaction vessel and a second position near an opening of said reaction vessel;
    a suction pump for applying a suction force to the suction tube sufficient to move a carrier contained in the reaction vessel out of the reaction vessel when said one end of the suction tube is in said second position, said one end of the suction tube comprising a suction nozzle having a diameter smaller than a diameter of the reaction vessel so that the suction nozzle of the suction tube is insertable into the reaction vessel and the carrier can be held at a tip portion of the suction nozzle by the suction force, said suction nozzle being connected to the suction pump through a waste liquid tank, whereby a test liquid contained in the reaction vessel is sucked into the waste liquid tank by means of the suction nozzle;
    a carrier discharge container, one end of the said suction tube being movable to a carrier discharge position adjacent said carrier discharge container; and
    a carrier container including a hopper for holding a plurality of carriers, a passage connected to a lower end of said hopper and having a curved portion and a flat portion, a vertical duct connected to an end of said passage, whereby carriers can be rolled down said passage in single row alignment into said vertical duct, said vertical duct limiting horizontal movement of said carriers at a carrier supply position, said first position of said nozzle comprising a location within said vertical duct whereby a carrier may be removed from said carrier container by said suction nozzle and a next adjacent carrier in said row alignment is automatically positioned by rolling down to said carrier supply position.

8. An apparatus according to claim 7, further comprising a colorimeter connected to said suction tube upstream of said waste liquid tank and a three-directional valve positioned between said colorimeter and said waste liquid tank, said three-directional valve selectively connecting said colorimeter to one of said waste liquid tank and an outlet to atmosphere.

* * * * *